United States Patent
Modi

(10) Patent No.: US 6,905,694 B1
(45) Date of Patent: Jun. 14, 2005

(54) HYDROPHOBICALLY MODIFIED POLYSACCHARIDE IN PERSONAL CARE PRODUCTS

(75) Inventor: Jashawant J. Modi, Hockessin, DE (US)

(73) Assignee: Hercules Incorporated, Wilmington, DE (US)

( * ) Notice: Subject to any disclaimer, the term of this patent is extended or adjusted under 35 U.S.C. 154(b) by 1072 days.

(21) Appl. No.: 08/855,779

(22) Filed: May 12, 1997

(51) Int. Cl.$^7$ ................................................. A61K 7/48
(52) U.S. Cl. .................... 424/401; 424/59; 424/701; 424/702; 424/706; 424/73
(58) Field of Search .............................. 424/401, 70.1, 424/59, 70.2, 70.6, 73, 70.13, 49, 402, 65; 514/944

(56) References Cited

U.S. PATENT DOCUMENTS

| | | | |
|---|---|---|---|
| 4,228,277 A | 10/1980 | Landoll | 539/90 |
| 4,663,159 A | 5/1987 | Brode, II et al. | 424/70 |
| 4,683,004 A | 7/1987 | Goddard | 106/170 |
| 4,826,970 A | 5/1989 | Rerd et al. | 536/66 |
| 4,845,207 A * | 7/1989 | T'Sas | 536/91 |
| 4,883,536 A | 11/1989 | Burdick | 106/194 |
| 4,902,733 A * | 2/1990 | Angerer | 524/44 |
| 4,904,772 A * | 2/1990 | Sau | 536/90 |
| 5,028,263 A | 7/1991 | Burdick | 106/194 |
| 5,080,717 A | 1/1992 | Young | 106/197.1 |
| 5,096,490 A | 3/1992 | Burdick | 106/171 |
| 5,100,658 A | 3/1992 | Bolich, Jr. et al. | 424/70 |
| 5,104,646 A | 4/1992 | Bolich, Jr. et al. | 424/70 |
| 5,106,609 A | 4/1992 | Bolich, Jr. et al. | 424/70 |
| 5,277,899 A * | 1/1994 | McCall | 424/71 |
| 5,288,484 A * | 2/1994 | Tashjian | 424/71 |

* cited by examiner

Primary Examiner—Jyothsna Venkat
(74) Attorney, Agent, or Firm—David Edwards

(57) ABSTRACT

A personal care composition is composed of:
(a) from about 0.1% to about 99% by weight of a vehicle system which comprises a hydrophobically modified nonionic water soluble polysaccharide polymer which comprises a water soluble polysaccharide polymer backbone and a hydrophobic moiety selected from the group consisting of 3-alkoxy-2-hydroxypropyl group wherein the allyl moiety is a straight or branch chain having 2–6 carbon atoms, $C_3$–$C_7$ alky aryl alkyl, alkyl aryl groups and mixtures thereof, wherein the ratio of the hydrophilic portion to the hydrophobic portion of the polymer is from about 2:1 to 1000:1, and
(b) at least one other personal care ingredient.

This compostion can be used in a wide range of personal care products such as shampoos, conditioners, hair coloring and styling agents, soaps, body washing agents, underarm products, lubricating agents, oral care products, denture adhesives, sunscreen agents, make-up products, and the like.

44 Claims, No Drawings

HYDROPHOBICALLY MODIFIED POLYSACCHARIDE IN PERSONAL CARE PRODUCTS

This invention relates to the use of hydrophobically modified polysaccharides in personal care products. More specifically, this invention relates to the use of such polysaccharides in personal care products where the alkyl moiety of the hydrophobe has 1–7 carbon atoms.

BACKGROUND OF THE INVENTION

Prior to the present invention, nonionic water soluble polysaccharides were used in personal care applications of shaving products, such as shaving creams and shaving gels, shampoos, shampoo conditioners, hair coloring systems, skin creams, lotions, facial cleansing products, under arm products, such as deodorants, antiperspirants, and mixtures thereof, lubricating gels, oral care products, such as toothpastes and mouth washes, denture adhesives, hair styling agents, such as hair gels and mousses, soaps, shower gels, body washes, make-up products, sun screen products, and the like. Widely used commercially available polysaccharides include nonionic water soluble polysaccharide ethers such as methyl cellulose (MC), hydroxypropylmethylcellulose (HPMC), hydroxyethylcellulose (HEC), hydroxypropylcellulose (HPC), and ethylhydroxyethylcellulose (EHEC) and hydroxypropyl (HP) guar, hydroxyethyl guar, and HP starch and other nonionic starch and guar derivatives. Also, hydrophobically modifed polysaccharides are used in personal care products. The use of these prior art polysaccharides in personal care products sometimes have processing difficulties such as compatibility with other ingredients, solubility with certain other ingredients, clarity (when needed) and stability under alkaline conditions of the personal care products. Also, hydrophobically modified polysaccharide are used in personal care products.

U.S. Pat. Nos. 5,106,609, 5,104,646, and 5,100,658 are examples of patents that disclose the use of hydrophobically modified nonionic cellulose ethers in personal care products. These patents disclose the use high molecular weight (i.e., 300,000 to 700,000) and long chain alkyl carbon substitution in the hydrophobe (i.e., 8 to 24 carbons) for use in hair and skin care cosmetics. Also, U.S. Pat. Nos. 4,228,277 and 4,352,916 describe hydrophobically modified cellulose ether derivatives, modified with long chain alkyl group substitution in the hydrophobe. U.S. Pat. No. 4,845,207 discloses a hydrophobically modified nonionic, water-soluble cellulose ether and U.S. Pat. No. 4,939,192 discloses the use of such ether in building compositions.

Certain of the prior art nonionic cellulose ethers have poor compatibility with salts or poor solubility in certain solvents used in personal care applications such as polyhydric alcohols while others are not tolerant to alkaline conditions. Hence, a need still exists in the personal care industry to have nonionic cellulose ethers that have good compatibility with salts, good solubility in certain solvents, and tolerant to alkaline conditions while producing products that do not have color problems, when desired.

SUMMARY OF THE INVENTION

1. A personal care composition comprising
   (a) from about 0.1% to about 990% by weight of a vehicle system which comprises a hydrophobically modified nonionic water soluble polysaccharide polymer which comprises a water soluble polysaccharide polymer backbone and a hydrophobic moiety selected from the group consisting of 3-alkoxy-2-hydroxypropyl group wherein the alkyl moiety is a straight or branch chain having 2–6 carbon atoms, $C_3$–$C_7$alkyl, aryl alkyl, alkyl aryl groups and mixtures thereof, wherein the ratio of the hydrophilic portion to the hydrophobic portion of the polymer is from about 2:1 to 1000:1, and
   (b) at least one other personal care ingredient.

DETAILED DESCRIPTION OF THE INVENTION

It has been surprisingly found that hydrophobically modified polysaccharide having a short chain alkyl group in the hydrophobe moiety have various advantageous properties over prior art water soluble polysaccharide and their derivatives in personal care products. Any water soluble polysaccharide or derivatives can be used as the backbone to form the hydrophobically modified polysaccharide of this invention. Thus, e.g., hydroxyethylcellulose (HEC), hydroxypropylcellulose (HPC), methylcellulose (MC), hydroxypropylmethylcellulose (HPMC), ethylhydroxyethylcellulose (EHEC), and methylhydroxyethylcellulose (MHEC) and, agar, dextran, locust bean gum, starch, guar and their nonionic derivatives can all be modified. The amount of nonionic substituent such as methyl, hydroxyethyl, or hydroxypropyl does not appear to be critical so long as there is a sufficient amount to assure that the ether is water soluble. The polysaccharides of this invention are nonionic having a sufficient degree of nonionic substitution to cause them to be water soluble and which are further substituted with a hydrocarbon radical having about 1 to 7 carbon atoms in an amount up to the amount which renders said polysaccharide less than 1% by weight soluble in water.

The preferred polysaccharide backbone is hydroxyethylcellulose (HEC). The HEC which is modified to function in this invention is a commercially available material. Suitable commercially available materials are marketed by the Aqualon Division of Hercules Incorproated, Wilmington, Del. U.S.A., under the trademark Natrosol®.

The short chain alkyl modifier can be attached to the polysaccharide backbone via an ether, ester, or urethane linkage. Preferred is the ether linkage as the reagents most commonly used to effect etherification are readily obtained, the reaction is similar to that commonly used for the initial etherification, and the reagents are usually more easily handled than the reagents used for modification via the other linkages. The resulting linkage is also usually more resistant to further reactions.

An example of the polysaccharides of the present invention is the 3-alkoxy-2-hydroxypropylhydroxyethylcellulose that is completely soluble in water at ambient temperature.

Typically, the 3-alkoxy-2-hydroxypropylhydroxyethylcellulose used in this invention has a hydroxyethyl molar substitution (M.S.). (The number of moles of hydroxyethyl substituent per cellulosic anhydroglucose unit in the cellulose molecule) of about 1.5 to 3.5. The alkylglycidyl radical is generally contained in an amount of about 0.05 to about 50 wt. %, preferably about 0.1 to about 25 wt. %, based on the dry weight of the substituted polymer. Preferably the alkyl group of the 3-alkoxy-2-hydroxypropyl group is a straight chain alkyl group having 2 to 6 carbon atoms. Exemplary modifying radicals are methyl-, ethyl-, propyl-, butyl-, pentyl- and 2-ethylhexylglycidyl ether.

Generally, the preferred method for preparing the ethers of this invention comprises slurrying the nonionic polysaccharide in an inert organic diluent such as a lower aliphatic alcohol, ketone, or hydrocarbon and adding a solution of alkali metal hydroxide to the resulting slurry at a low temperature. When the ether is thoroughly wetted and the reaction is continued, with agitation, until complete. Residual alkali is then neutralized and the product is recovered, washed with inert diluents, and dried. The etherification can also be affected with $C_3$ to $C_7$ halide or halohydride but these are sometimes less reactive, less efficient, and more corrosive so it is preferred to use the epoxide.

Substantially the same procedure is used to attach the hydrocarbon modifier via the ester or urethane linkage. Conventional slurry methods of reacting this type of modifier with polysaccharide, i.e., without the alkali, are ineffective. The alkali step is required in order to assure that the polysaccharide is swollen to the point that the modifier can react substantially uniformly on all polysaccharide molecules throughout. If reaction is not substantially uniform through the polysaccharide mass, the improved solubility and cloud point properties are not realized.

The hydrophobically modified polysaccharide of this invention show significantly improved salt tolerance in high salt systems compared to hydrophobically modified polysaccharide that are commercially marketed for personal care applications. In addition, these polysaccharides have improved solubility in solvent systems used in personal care applications compared to hydrophobically modified polysaccharide commercially marketed in the personal care industry. This salt tolerance of the polymer is determined by measuring the cloud point in a 15% sodium chloride solution. The cloud point is a temperature at which in a clear solution starts to become cloudy and the polymer starts to precipitate out.

The hydrophobically modified hydroxyalkylcellulose of the present invention is an essential ingredient of the vehicle system of personal care products. In some products, it can be substantially the only ingredient needed for this vehicle system. Another ingredient that may be in the vehicle system is a surfactant that can be either soluble or insoluble in the composition. A compatible solvent may also be used in the vehicle system that can be either a single solvent or a blend of solvents.

Examples of the surfactants are anionic, nonionic, cationic, switterionic, or amphoteric type of surfactants. The surf can be insoluble (or soluble) in the present invention and (when used) is present in the composition of from 0.01 to about 25% by weight of the composition.

Synthetic anionic surfactants include alkyl and alkyl ether sulfates. Specific examples of alkyl ether sulfates which can be used in the present invention are sodium coconut alkyl trimethylene glycol ether sulfate; sodium tallow alkyl trimethylene glycol ether sulfate; sodium tallow alkyl hexaoxyethylene sulfate; sodium tallow alkyl diethylene glycol ether sulfate; and sodium tallow alkyl sulfate.

Nonionic surfactants, can be broadly defined as compounds containing a hydrophobic moiety and a nonionic hydrophilic moiety. Examples of the hydrophobic moiety can be alkyl, alkyl aromatic, dialkyl siloxane, polyoxyalkylene, and fluoro-substituted alkyls. Examples of hydrophilic moieties are polyoxyalkylenes, phosphine oxides, sulfoxides, amine oxides, and amides.

Cationic surfactants useful in vehicle systems of the compositions of the present invention, contain amino or quaternary ammonium hydrophilic moieties which are positively charged when dissolved in the aqueous composition of the present invention.

Zwitterionic surfactants are exemplified by those which can be broadly described as derivative of aliphatic quaternary ammonium, phosphonium, and sulfonium compounds, in which the aliphatic radicals can be straight or branched chain, and wherein one of the aliphatic substituents contains from about 8 to about 18 carbon atoms and one contains as anionic water-solubilizing group, e.g., carboxy, sulfonate, sulfate, phosphate, or phosphonate.

Examples of amphoteric surfactants which can be used in the vehicle systems of the compositions of the present invention are those which are broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group, e.g., carboxy, sulfonate, sulfate, phosphate, or phosphonate.

The water-soluble (or insoluble) surfactant is used with the polysaccharide of the present invention at from about 0.01% to about 25% of the composition.

According to the present invention, the solvent used in the vehicle system should be compatible with the other components in the present composition. Examples of the solvents used in the present invention are water, water-lower alkanols mixtures, and polyhydric alcohols having from 3 to 6 carbon atoms and from 2 to 6 hydroxyl groups. Preferred solvents are water, propylene glycol water-glycerine, sorbitol-water, and water-ethanol. The solvent (when used) in the present invention is present in the composition at a level of from 0.1% to 99% by weight of the composition.

The active personal care component is optional because the vehicle system can be the active ingredient component. An example of this is the use of the vehicle system in a denture adhesive as either a cream or powder. However, when an active personal care ingredient is needed, it must provide some benefit to the user's body. Example of substances that may suitably be included in the personal care products according to the present invention are as follows:

1) Perfumes, which give rise to an olfactory response in the form of a fragrance and deodorant perfumes which in addition to providing a fragrance response can also reduce body malodor;

2) Skin coolants, such as menthol, menthyl acetate, menthyl pyrrrolidone carboxylate N-ethyl-p-menthane-3-carboxamide and other derivatives of menthol, which give rise to a tactile response in the form of a cooling sensation on the skin;

3) Emollients, such as isosiopropylmyristate, silicone oils, mineral oils and vegetable oils which give rise to a tactile response in the form of an increase in skin lubricity;

4) Deodorants other than perfumes, whose function is to reduce the level of or eliminate micro flora at the skin surf, especially those responsible for the development of body malodor. Precursors of deodorants other than perfume can also be used;

5) Antiperspirant actives, whose function is to reduce or eliminate the appearance of perspiration at the skin surface;

6) Moisturizing agents, that keeps the skin moist by either adding moisture or preventing from evaporating from the skin;

7) Cleansing agents, that removes dirt and oil from the skin;

8) Sunscreen active ingredients, that protect the skin and hair from UV and other harmful light rays from the sun.

In accordance with this invention a therapeutically effective amount will normally be from 0.01 to 10% by weight, preferable 0.1 to 5% by weight of the composition;

9) Hair treatment agents, that conditions the hair, cleans the hair, detangles hair, acts as styling agent, anti-dandruff agent, hair growth promoters, hair dyes and pigments, hair perfumes, hair relaxer, hair bleaching agent, hair moisturer, hair oil treatment agent, and antifrizzing agent;
10) Oral care agents, such as dentifrices and mouth washes, that cleans, whiten, deodorizes and protects the teeth and gum;
11) Denture adhesives that provide adhesion properties to dentures;
12) Shaving products, such as creams, gels and lotions and razor blade lubricating strips;
13) Tissue paper products, such as cleansing tissues;
14) Beauty aids, such as foundation powders, lipsticks, and eye care.

The above list is only examples and is not a complete list of active ingredients that can be used in personal care compositions. Other ingredients that are use in these type of products are well know in the industry. In addition to the above ingredients conventionally used in products for personal care, the composition according to the present invention can optionally also include ingredients such as a colorant, preservative, antioxidant, vitamins, activity enhance, spermacidals, emulsifiers, viscosifying agents (such as salts, i.e., NaCl, $NH_4Cl$ & KCl), and fats and oils.

The vehicle systems and personal care compositions of the present invention can be made using conventional formulation and mixing techniques. Methods of making various types of personal care compositions are described more specifically in the following examples. The following examples are merely set forth for illustrative purpose, but it to be understood that other modifications of the present invention within the skill of artisans in the personal care industry can be made without departing from the spirit and scope of the invention.

EXAMPLE 1

Opaque Liquid Soap Formula

| Ingredients | Weight % |
|---|---|
| Water | 75.88 |
| Sodium C14–C16 olefin sulfonate, 40% active | 7.50 |
| Sodium lauroyl sarcosinate, 30% active | 6.66 |
| Cocamidopropyl betaine, 35% active | 6.66 |
| Glycol stearate | 1.00 |
| HMHEC1* | 0.80 |
| Propylene glycol | 0.50 |
| Glycerin | 0.50 |
| Tetrasodium EDTA | 0.30 |
| Stearalkonium chloride | 0.10 |
| Methylparaben | 1.10 |
| | 100.00 |

*This compound is 3-butoxy-2-hydroxypropylhydroxyethylcellulose, that has aqueous viscosity at 25° C. of a minimum of 2500 cps at 1%, measured on a brookfield LVTD Viscometer, and a cloud point of about 72°–78° C., that is treated with glyoxal.

Procedure

1. The HMHEC1* was dispersed in water. pH was raised to about 8.0–8.5 to dissolve the polymer and mixed for 45 minutes. The methylparaben was added to the finished solution.

2. While slowly stirring the water-soluble polymer solution, the stearalkonium chloride, olefin sulfonate, and glycol stearate were added. The mixture was heated to 80° C. until all of the glycol stearate was melted and the solution had turned opaque.

3. The remaining ingredients were added while cooling the solution slowly to room temperature.

4. The color and fragrance were added.

EXAMPLE 2

Toilet Soap Formula

| Ingredients | Weight % |
|---|---|
| Water | 65.70 |
| Sodium C14–C16 olefin sulfonate | 20.00 |
| Sodium lauroyl sarcosinate | 10.00 |
| Cocamide MEA | 3.00 |
| HMHEC3* | 0.75 |
| Natrosol 250HR | 0.25 |
| Disodium EDTA | 0.20 |
| Methylparaben | 0.10 |
| | 100.00 |

*This compound is 3-butoxy-2-hydroxypropylhydroxyethy cellulose, that has aqueous viscosity at 25° C. of a minimum of 2000 cps at 1%, measured on a Brookfield LVTD Viscometer, and a cloud point of about 62°–68° C. with glyoxal treatment.

Procedure

1. The HMHEC3* and Natrosol 250HR product were dispersed in water. The pH was raised to about 8.0–8.5 to dissolve the polymer and mixed for 45 minutes. The methylparaben was added to the finished solution.

2. In a separate vessel, the surfactants were combined, heated to 80° C., and mix until homogeneous.

3. The surfactant solution was added to the water-soluble polymer solution and mixed until well blended.

4. The disodium EDTA was added and cooled to room temperature.

Source and Description of Products Used in Examples 1 and 2

| Generic or CTFA Adopted Name | Trademark | Supplier |
|---|---|---|
| Stearalkonium chloride | Ammonyx 4002 | Stepan Chemical Company Northfield, Illinois |
| Sodium C14–16 olefin sulfonate | Bio-Terge AS-40 | Stepan Chemical Company Northfield, Illinois |
| Sodium lauroyl sarcosinate | Hamposyl L-30 | W. R. Grace & Company Nashua, New Hampshire |
| Cocamidopropyl betaine | Lexaine C | Inolex Chemical Company Philadelphia, Pennsylvania |
| Cocamide MEA | Monamid CMA | Mona Industries Inc. Paterson, New Jersey |
| Tetrasodium EDTA | Perma Kleer 100 | Stepan Chemical Company Northfiel, Illinois |
| | HMHEC 3 | Hercules Incorporated Wilmington, Delaware |
| | HMHEC 1 | Hercules Incorporated Wilmington, Delaware |
| | Natrosol 250HR | Hercules Incorporated |

EXAMPLE 3

Baby Hair Conditioner Formula

| Ingredients | Weight % |
| --- | --- |
| HMHEC3 | 1.0 |
| Water | 74.1 |
| Cetrimonium chloride (25%) | 12.2 |
| Lauramine oxide (30%) | 10.2 |
| Polyquaternium-17 (62%) | 1.5 |
| Propylene glycol | 1.0 |
| Perfume, preservative | q.s. to 100.0 |

Procedure

1. The HMHEC3 was dispersed in water with good agitation and mixed until fully dissolved.
2. The remaining ingredients were added in the order listed, mixing well between additions.

EXAMPLE 4

Pearlescent Cream Rinse Formulation

| Ingredients | Weight % |
| --- | --- |
| Phase A. | |
| HMHEC1 | 1.0 |
| Natrosol 250HHR | 0.3 |
| Water | 82.3 |
| Phase B. | |
| Stearalkonium chloride (25%) | 10.1 |
| Propylene glycol | 1.5 |
| Glycol stearate | 1.5 |
| Oleth-20 | 1.5 |
| Polyquaternium-17 (62%) | 1.8 |
| Perfume, preservative | q.s. to 100.0 |

Procedure

1. The HMHEC1 was dispersed in water with good agitation, pH was raised to 8.0–8.5, the dispersion was mixed until fully dissolved.
2. In a separate vessel, the stearalkonium chloride and propylene glycol were mixed together and heated to 80° C.
3. The other ingredients listed in Phase B were added in the order listed to the mixture of stearalkonium chloride and propylene glycol and mixed well between each addition.
4. The surfactant mixture was added to the HMHEC1 solution, mixed well, and cooled to 35° C.
5. The perfume and preservative were then added to form the final formulation.

Raw Materials and Their Sources for Examples 3 and 4

| CTFA Adopted Name | Trademark | Supplier |
| --- | --- | --- |
| Quaternium-48 | Adogen 470 | Sherex Chemical Co., Inc. Dublin, Ohio |
| Oleth-20 | Emulphor ON-870 | Rhone-Poulenc Cranbury, New Jersey |
| Hydrolyzed animal protein | Lexein X-250 | Inolex Chemical Company Philadelphia, Pennsylvania |
| Polyquaternium-17 | Mirapol AD-1 | Rhone-Poulenc Cranbury, New Jersey |
| Cocamidopropylamine oxide | Ammonyx CDO | Stepan Company Northfield, Illinois |
| Lauramine oxide | Ammonyx LO | Stepan Company Northfield, Illinois |
| Cetrimonium chloride | Varisoft E228 | Sherex Chemical Co., Inc. Dublin, Ohio |
| Stearalkonium chloride | Varisoft SDC | Sherex Chemical Co., Inc. Dublin, Ohio |
| HMHEC1 | | Hercules Incorporated |
| Natrosol 250HHR | | Wilmington, Delaware |

EXAMPLE 5

Gentle Everyday Shampoo

| Ingredients | Weight % |
| --- | --- |
| Distilled water | q.s. to 100.00 |
| Sodium laureth sulfate, 28% | 19.60 |
| Cocamidopropyl betaine, 35% | 11.00 |
| Sodium lauroyl sarcosinate, 30% | 9.60 |
| PEG-150 distearate | 2.90 |
| HMHEC3 | 1.10 |
| Methylchloroisothiazolinone and Methylisothiazolinone, 1.5% | 0.08 |

Procedure

1. The HMHEC3 was dispersed by adding to the vortex of well-agitated, heated to 60–70° C., water in a vessel.
2. The surfactants, one at a time, were added to the vessel while mixing well between each addition.
3. The PEG-150 distearate was then added to the vessel, nixed until dissolved, and then the heat was turned off.
4. When temperature cooled to 40° C. or below, the fragrance and preservative were added to the formulation.

Raw Materials and Their Sources

| CTFA Adopted Name | Trademark | Supplier |
| --- | --- | --- |
| Cocamidopropyl betaine | Lexaine C | Inolex Chemical Co. Philadelphia, Pennsylvania |
| Methylchloroiso-thiazolinone and Methylisothiazolinone | Kathon CG | Rohm & Haas Co. Philadelphia, Pennsylvania |
| Methyl paraben | Methyl Parasept | Kalama Chemicals, Inc. Garfield, New Jersey |
| PEG-150 distearate | Witconol L32-45 | Witco Chemical Oakland, New Jersey |
| Sodium laureth sulfate, 28% | Steol 4N | Stepan Company Northfield, Illinois |
| Sodium lauroyl sarcosinate | Hamposyl L-30 | W. R. Grace & Co. Lexington, Massachusetts |

EXAMPLE 6

Hand and Body Lotion

| Part | Ingredients | Weight % |
| --- | --- | --- |
| A | HMHEC1 | 0.50 |
| | Distilled water | 78.25 |
| | Glycerin, USP | 2.00 |

-continued

Hand and Body Lotion

| Part | Ingredients | Weight % |
|---|---|---|
| B | Glycol sterate | 2.75 |
|  | Stearic acid | 2.50 |
|  | Mineral oil | 2.00 |
|  | Acetylated lanolin | 0.50 |
|  | Cetyl alcohol | 0.25 |
| C | Distilled water | 10.00 |
|  | Triethanolamine | 0.50 |
| D | Propylene glycol and diazolidinyl urea and Methylparaben and propylparaben | 0.75 |

Procedure

1. The HMHEC1 was dispersed by adding to the vortex of well-agitated water in a vessel from Part A. The glycerin was then added with continued mixing and heated to 80° C.

2. In a separate vessel, the Part B ingredients were blended together, heated to 80° C., and mixed well.

3. The Part A and Part B components were mixed together while agitating vigorously to produce an emulsion. This emulsion was maintained at a temperature of 80° C. with constant stirring.

4. Then, the Part C ingredients were added to the emulsion and the mixture was mixed continuously while cooling to 40° C.

5. The Part D (preservative) component was added to this new emulsion and was mixed well.

6. The formulation was then cooled.

Materials and Their Suppliers

| CTFA Adopted Name | Trademark | Supplier |
|---|---|---|
|  | HMHEC1 | Hercules Incorporated Wilmington, Delaware |
| Glycol stearate | Cyclochem EGMS | Rhone-Poulenc Cranbury, New Jersey |
| Stearic acid | Industrene 5016 | Witco Corporation Dublin, Ohio |
| Acetylated lanolin | Acylan | Croda Inc. Parsippany, New Jersey |
| Cetyl alcohol | Crodacol C-70 | Croda Inc. Parsippany, New Jersey |
| Propylene glycol, diazolidinyl urea, Methylparaben and propylparaben | Germaben II | Sutton Laboratories Chatham, New Jersey |

EXAMPLE 7

Shaving Cream

| Ingredients | Amount, g |
|---|---|
| Deionized water | 633.6 |
| Sodium hydroxide (24.6% solution) | 9.6 |
| Potassium hydroxide (34.2% solution) | 34.2 |
| Stearic acid, double pressed | 71.6 |
| Coconut acid | 10.0 |
| Propylene glycol | 27.0 |
| Lauramide DEA | 10.0 |
| Coconut oil | 2.5 |

-continued

Shaving Cream

| Ingredients | Amount, g |
|---|---|
| Tallow glycerides | 30.0 |
| Preservative | 5.0 |
| HMHEC3 slurry | 166.5 |
| Total | 1000.0 |

Procedure

To prepare the shaving cream concentrate, the sodium hydroxide and potassium hydroxide were added to the deionized water in a vessel at room temperature. The temperature of the vessel was then raised to 75° C. and stirred for 5 minutes. The stearic acid and coconut acid were separately pre-melted and then each was added to the caustic/water mixture and then stirred for 30 minutes followed by cooling to 55° C. One at a time, the propylene glycol, lauramide DEA (melted), coconut oil, tallow glycerides (melted), and preservative were added to the vessel and stirred for 15 minutes and allowed to cool. The HMHEC3 slurry was then added and cooled to room temperature while stirring.

1.0 g of HMHEC3 was added to 165.5 g of well agitated water to prepare a slurry. The slurry was added immediately to the formulation. The polymer can also be added as a solution. To dissolve the polymer, the slurry's pH was adjusted to 8.0–8.5 and mixed for 45 minutes or until dissolved.

The concentrate (225 g) was weighed into a standard 12-oz shaving cream can. The can was then sealed with a valve assembly using laboratory canning equipment and charged with 9.0 g of propellant.

List of Ingredients and Their Suppliers

| CTFA Adopted Name | Trademark | Supplier |
|---|---|---|
|  | HMHEC3 | Hercules Incorporated Wilmington, Delaware |
| Stearic acid | Industrene 5016 | Witco Corporation Memphis, Tennessee |
| Coconut acid | Industrene 328 | Witco Corporation Memphis, Tennessee |
| Lauramide DEA | Standamid LD | Henkel Corporation Ambler, Pennsylvania |
| Coconut oil | Coconut oil | Sigma Chemical Co. St. Louis, Missouri |
| Tallow glycerides | Peacock Acidless Tallow | Geo. Pfau's Sons Co. Jeffersonville, Indiana |
| Sorbitol | Sorbo (70% active) | ICI Americas, Inc. Wilmington, Delaware |
| Propylene glycol (and) Diazolidinyl urea (and) Methylparaben (and) Propylparaben | Germaben II | Sutton Laboratories Chatham, New Jersey |
| 88/12 Isobutane/propane | A-46 Propellant | Aeropres Corporation Shreveport, Louisiana |
| Propylene glycol | Propylene Glycol | Eastman Chemical Co. Rochester, New York |

EXAMPLE 8

Standard Cream Toothpaste with HMHEC2

|      | Ingredient                  | wt %    |
|------|-----------------------------|---------|
| I.   | HMHEC2*                     | 0.75[1] |
|      | Glycerin 100%               | 13.00   |
|      | Sorbitol (70% solids)       | 16.86   |
|      | Distilled water             | 14.71[2]|
| II.  | Dicalcium phosphate, anhydrous | 45.00 |
| III. | Tetra sodium pyrophosphate  | 0.42    |
|      | Sodium saccharin            | 0.20    |
|      | Sodium monofluorophosphate  | 0.76    |
|      | Sodium benzoate             | 0.50    |
|      | Distilled water             | 6.25    |
| IV.  | Flavor                      | 0.55    |
|      | Sodium lauryl sulfate       | 1.00    |
|      |                             | 100.00  |

[1] Correct polymer weight for moisture content.
[2] For water: Adjust the amount of water for moisture in the polymer.
*HMHEC2 is 3-butoxy-2-hydroxypropylhydroxyethylcellulose that has an aqueous viscosity at 25° C. of a minimum of 2000 cps at 1% measured on a Brookfield LVTD Viscometer and has a cloud point about 62°–68° C. without glyoxal treatment.

1) The salts of Part m were added to the water in a vessel while stirring and heated to about 60° C. to dissolve. The vessel was covered during heating to prevent moisture loss.
2) Part I. The glycerine was weighed into a beaker and the polymer was dispersed in the glycerine while stirring for about 5 minutes or until adequately dispersed. Sorbitol was added and the mixture was continuously stirred for another 10 minutes. water was added and stirred for an additional 15 to 30 minutes making sure that the polymer was completely hydrated (no gels). A warm salt solution was added while stirring continuously for an additional 15 minutes or until homogenous (no lumps or gels). This mixture was then transferred to a toothpaste mixer (Ross double planetary mixer).
3) Part II. The DCP and water were added to a mixer and mixed for 10 min. at a low speed to completely wet the DCP. The mixer was then opened and the DCP was scraped from the beaters and bowl sides. The mixer was then closed and a vacuum was applied. The mixer was run on high speed under vacuum for 20 minutes or until the DCP had a smooth consistency.
4) Part IV. The SLS was added to the mixer and mixed for 5 minutes at low speed without vacuum. The flavor was added to the mixer and mixed for 2 min. at low speed. The mixer was then opened and the beaters and bowl sides were scraped down. The mixer was closed and a vacuum was applied and mixed at medium speed for 15 minutes, observing for foaming.
5) The mixer was then shut off and the vacuum was broken and the formulation was packed out as a paste.

EXAMPLE 9

Standard Cream Toothpaste with HMHEC2

|      | Ingredient                 | wt %    |
|------|----------------------------|---------|
| I.   | HMHEC2                     | 0.75[1] |
|      | CMC 7MF (Hercules Incorporated) | 0.25[1] |
|      | Glycerin 100%              | 13.00   |
|      | Sorbitol (70% solids)      | 16.86   |
|      | Distilled water            | 14.46[2]|
| II.  | Dicalcium phosphate, anhydrous | 45.00 |
| III. | Tetra sodium pyrophosphate | 0.42    |
|      | Sodium saccharin           | 0.20    |
|      | Sodium monofluorophosphate | 0.76    |
|      | Sodium benzoate            | 0.50    |
|      | Distilled water            | 6.25    |
| IV.  | Flavor                     | 0.55    |
|      | Sodium lauryl sulfate      | 1.00    |
|      |                            | 100.00  |

[1] Correct polymer weight for moisture content.
[2] For water: Adjust the amount of water for moisture in the polymer.

1) Begin with Part III. The salts were added to the water while stirring and heated to about 60° C. to dissolve. The salt and water mixture was covered during heating to prevent moisture loss.
2) Part I. Glycerine was weighed into a beaker and the polymer was dispersed in the glycerine while stirring. This mixture was stirred for 5 minutes or until adequately dispersed. Sorbitol was added the this dispersion and was continuously stirred for another 10 minutes. Water was added and stirred for 15 to 30 minutes making sure that the polymer was completely hydrated (no gels). Then warm salt solution was added while stirring and was continuously stirred for 15 minutes or until homogenous (no lumps or gels). This mixture was then transferred to a toothpaste mixer (Ross double planetary mixer).
3) Part II. DCP was added to the mixer and was mixed for 10 min. at a low speed to completely wet the DCP. The mixer was then opened and beaters and bowl sides were scraped down. The mixer was closed and a vacuum was applied. The mixer was then run on high speed under vacuum for 20 minutes or until the mixture was smooth.
4) Part IV. SLS was added and mixed for 5 minutes at low speed without vacuum. Flavor was add and mixed for 2 min. at low speed and the mixer was opened and beaters and bowl sides were scraped down. The mixer was closeed and a vacuum was applied. The mixer was run on medium speed for 15 minutes; observe for foaming.
5) The mixer turned off and the vacuum was broken. The blend from the mixer was packed out as a paste.

EXAMPLE 10

Cream Toothpaste with HMHEC1

|      | Ingredient                  | %       | wt (g)  |
|------|-----------------------------|---------|---------|
| I.   | HMHEC1                      | 0.75    | 15.00   |
|      | Glycerine 100%              | 13.00   | 260.00  |
|      | Sorbitol (70%)              | 16.86   | 337.20  |
|      | Distilled water             | 16.96[2]| 339.2   |
| II.  | Dicalcium phosphate, dihydrate | 45.00 | 900.00  |
| III. | Tetra sodium pyrophosphate  | 0.42    | 8.40    |
|      | Sodium monofluorophosphate  | 0.76    | 15.20   |
|      | Sodium saccharin            | 0.20    | 4.00    |
|      | Sodium benzoate             | 0.50    | 10.00   |
| IV.  | Flavor                      | 0.55    | 11.00   |

-continued

| | Cream Toothpaste with HMHEC1 | | |
|---|---|---|---|
| | Ingredient | % | wt (g) |
| V. | Sodium lauryl sulfate | 1.00 | 20.00 |
| | Distilled water | 4.00 | 80.00 |
| | | 100.00 | 2000.00 |

[1]correct polymer weight for moisture content.
[2]Adjust the water level for polymer moisture correction.

1) Part I. The glycerine was weighed into a beaker. The polymer was dispersed in the glycerine in a Jiffy mixer while stirring. This glycerine and polymer mixture was stirred for 5 minutes or until adequately dispersed. Sodium saccharin and sodium benzoate were added to the dispersion and mixed for an additional 5 min. Sorbitol was then added and mixed for 5 min. Water was then added and stirred for 30 min. After stirring for the 30 min., total weight of beaker was recorded and stirred again. The solution was heated to 80° C. and mixed for 15 min. at 80° C. The beaker was reweighed and the weight was adjusted for any weight loss due to evaporation. The the contents of the beaker then was transferred to a Ross planetary vacuum mixer.
2) During the polymer hydration period, Part V was begun. SLS was added to the water while stirring and dissolved by warming to ~50° C. in a water bath. if lumping occurred, the process was restarted.
3) Part II. DCP was added to a mixer and was mixed for 10 min. on a low speed to completely wet the DCP. The mixer was stopped and the beaters and bowl sides were scraped down. The mixer was then closed and a vacuum was applied. The mixer was run on high speed under vacuum for 20 minutes or until smooth paste.
4) TSPP was added to the mixer and was mixed for 5 min. Then, SMFP as added and mixed for 5 min. The saccharin was added and mix for 5 mins. The sodium benzoate was added and mix 5 mins. on low speed followed by 10 min. on medium speed or until smooth.
5) Part IV. The SLS was added and mixed for 5 minutes on low speed without vacuum. The flavor was added and mixed for 2 min at low speed. The mixer was opened and the beaters and bowl sides were scraped down. The mixer was closed and a vacuum was applied and mixed at medium speed for 15 minutes, observe for foaming.
6) The mixer speed was reduced and shut off after awhile and the vacuum was broken. The mixer content was then packed out as a paste.

EXAMPLE 11

| | Cream Toothpaste with HMHEC1 | | |
|---|---|---|---|
| | Ingredient | % | wt (g) |
| I. | HMHEC1 | 0.75 | 15.00 |
| | Genuvsco TPH1 | 0.25 | 5.00 |
| | (Hercules Incorporated) | | |
| | Glycerine 100% | 13.00 | 260.00 |
| | Sorbitol (70%) | 16.86 | 337.20 |
| | Distilled water | 16.71[2] | 334.2 |
| II. | Dicalcium phosphate, dihydrate | 45.00 | 900.00 |
| III. | Tetra sodium pyrophosphate | 0.42 | 8.40 |

-continued

| | Cream Toothpaste with HMHEC1 | | |
|---|---|---|---|
| | Ingredient | % | wt (g) |
| | Sodium monofluorophosphate | 0.76 | 15.20 |
| | Sodium saccharin | 0.20 | 4.00 |
| | Sodium benzoate | 0.50 | 10.00 |
| IV. | Flavor | 0.55 | 11.00 |
| V. | Sodium lauryl sulfate | 1.00 | 20.00 |
| | Distilled water | 4.00 | 80.00 |
| | | 100.00 | 2000.00 |

[1]correct polymer weight for moisture content.
[2]Adjust the water level for polymer moisture correction.

1) Part I. glycerine was weighed into a beaker. Polymer was dispersed in glycerine in a Jiffy mixer while stirring and was stirred for 5 minutes or until adequately dispersed. Sodium saccharin and sodium benzoate were added to the mixer and mix for 5 min. Sorbitol was then added to the mixer and mixed for 5 min. water was then added and stir for 30 min. After stirring for 30 min., the total weight of beaker was recorded. The solution was then heated to 80° C., mixed for 15 min. at 80° C., and reweighed. The weight was adjusted for any weight loss due to evaporation. The mixture was transferred to a Ross planetary vacuum mixer.
2) During the polymer hydration period, Part V was begun. SLS was added to the water while stirring. The SLS was dissolved by warming to ~50° C. in a water bath. If lumping occurred, the process was restarted.
3) Part II. DCP was added to the mixer and mixed for 10 min. at a low speed to completely wet the DCP. The mixer was stopped and beaters and bowl sides were scraped down. The mixer was closed, a vacuum was applied, and was mixed on high speed under vacuum for 20 minutes or until the paste became smooth.
4) TSPP was added to the mixer and mixed for 5 min. Next the SMFP was added and mixed for 5 min. The saccharin was then added and mixed for 5 mins. Next, the sodium benzoate was added and mixed for 5 mins. on low speed followed by 10 min. on medium speed or until smooth.
5) Part IV. The SLS was added and mixed for 5 minutes on low speed without vacuum. Then, the flavor was added and mixed for 2 min at low speed. The mixer was then opened and the beaters and bowl sides were scraped down. The mixer was then closed and a vacuum was applied. The mixer was run at medium speed for 15 minutes, observe for foaming.
6) mixer's speed was reduced gradually and finally shut off and the vacuum was broken. The content of the mixer was packed out as a paste.

EXAMPLE 12

| Lubricating Jelly (or liquid) |
|---|
| FORMULATION 1 |
| 2.2% Nonoxynol 9 |
| 3.0% HMHEC2 |
| 94.9% Propylene Glycol |
| 0.1% Methyl parasept |
| FORMULATION 2 |
| 2.2% Nonoxynol 9 |

-continued

| Lubricating Jelly (or liquid) |
| --- |
| 1.5% HMHEC2 |
| 1.5% Natrosol 250HHX (Hercules Incorporated) |
| 24.9 Water |
| 70.9% Propylene Glycol |
| 0.1% Methyl parasept |
| FORMULATION 3 |
| 4.0% HMHEC2 |
| 95.9% Propylene Glycol |
| 0.1% Methyl parasept |
| FORMULATION 4 |
| 2.0% HMHEC2 |
| 1.5% Klucel HF (Hercules Incorporated) |
| 94.9% Propylene Glycol |
| 0.1% Methyl parasept |
| FORMULATION 5 |
| 0.5% HMHEC2 |
| 0.5% Klucel HF |
| 10.0% mineral oil |
| 34.9% Propylene Glycol |
| 54.0% water |
| 0.1% Methyl parasept |

The polymer was dispersed into vortex of vigorously agitated propylene glycol and/or mineral oil and mixed for ten minutes. Water was added. Next the temperature was raised to 90° C. and mixed for one hour and then was gradually cooled to about 25° C. while mixing slowly. Nonoxynol and preservative (as required) were added while mixing. Then the formualtionr was deaerated and was packed out.

EXAMPLE 13

| Denture Adhesive |
| --- |
| FORMULATION 1 |
| 25.0% CMC 7H3SXF (Hercules Incorporated) |
| 25.0% HMHEC2 |
| 45.0% Petrolatum (Snow White from Penerico) |
| 5.0% Mineral oil (Drakeol 9 from Penerico) |
| FORMULATION 2 |
| 50.0% HMHEC2 |
| 45.0% Petrolatum (Snow White from Penerico) |
| 5.0% Mineral oil (Drakeol 9 from Penrico) | petrolatum was preheated to 60° C. in a vessel and mineral oil was added and mixed for five minutes. Polymer was then added to agitated liquid in the vessel and continued to mix for 30 minutes. The formulation was then transferred to a packout container and allowed to cool to about 25° C.

EXAMPLE 14

Clear Stick Antiperspirant

A two phase method was used to prepare the dear stick antiperspirant as follows:

Phase I

About 65% of the total propylene glycol used (excluding that which is part of the antiperspirant salt solution) was charged to a reaction vessel. HMHEC1 was added to the vessel and stirred well until dissolved. The vessel was heated to dissolve the polymer. Once the polymer was dissolved, the solution was heated to 110° C.–115° C., and the dibenzylidine sorbitol was added and mixed until completely dissolved. This Phase I solution was then cooled to about 100° C.

Phase II

About 35% of the total propylene glycol used (excluding that which is part of the antiperspirant salt solution) was added to the another vessel, stirred and heated to about 60–70° C. The $Na_4EDTA$ was added and mixed well to form a slurry. The antiperspirant salt solution was added next to this vessel and the solution was mixed well until it becomes clear and homogeneous. The emollients, dimethicone copolymer, was added and the Phase II solution was mixed until it became clear.

Combined Phase:

Phase II was added to Phase I while mixing and cooled to 80° C. Optionally a fragrance would be added at this point and allowed to mix well. The product was poured into a 1 oz. glass jars and allowed to cool overnight. After cooling overnight, the samples were tested for physical and chemical properties.

Equipment used:

Two 400 ml glass beakers, oil bath, clamps, mechanical stirrer, Jiffy stirrer and thermometer, and a covering to prevent contamination, such as plastic wrap.

| Total Formulation for this Example | |
| --- | --- |
| 1. Propylene glycol | 49.70 g |
| 2. Al/Zr tetrachlorohydrate-gly | 36.60 g* |
| 3. Dibenzylidene sorbitol | 0.50 g |
| 4. HMHEC1 | 0.30 |
| 5. Sodium EDTA | 0.20 |
| 6. Dimethicone copolymer (ABIL B 8851) | 0.25 |
| 7. Fragrance (optional) | 1.25 |
| Phase I: | |
| Polypropylene glycol | 32.30 g |
| Dibenzylidene sorbitol | 0.50 g |
| HMHEC1 | 0.30 g |
| Phase II: | |
| Polypropylene glycol | 17.40 g |
| Al/Zr tetrachlorohydrate-gly | 36.60 g |
| Sodium EDTA | 0.20 g |
| Dimethicone copolymer | 0.25 g |
| Fragrance (optional) | 1.25 g |

*30% active solution.

Chemicals, Suppliers:

1. Propylene glycol (EM Science UPS grade)
2. Al/Zr tetrachlorohydrate-gly (Westwood Chemical Co.) Westchlor A2Z 8160 30% PG solution.
3. Dibenzylidene sorbitol (Milliken Chemicals) Millithix 925.
4. HMHEC1 (Hercules Incorporated)
5. Sodium EDTA (Aldrich #5403EJ)
7. Dimethicone copolymer (Goldschmidt Chemical) ABIL B 8851
8. Fragrance

What is claimed:

1. A personal care composition comprising:
    a. from about 0.1% to about 99% by weight of a vehicle system which comprises a hydrophobically modified nonionic water soluble polysaccharide polymer having a hydrophilic portion which comprises a water soluble polysaccharide polymer backbone and a hydrophobic moiety selected from the group consisting of $C_3$–$C_7$ alkyl, aryl alkyl, alkyl aryl groups and mixtures thereof, wherein the ratio of the hydrophilic portion to the hydrophobic portion of the polymer is from about 2:1 to 1000:1, and b. at least one active personal care ingredient, wherein the composition is an oil-in-water or water-in-oil emulsion.

2. The composition of claim 1 wherein the composition also comprises from about 0.01% to about 25% by weight of the personal care composition of a surfactant.

3. The composition of claim 2 wherein the surfactant is selected from the group consisting of anionic, nonionic, cationic, zwitterionic, and amphoteric, mixtures thereof.

4. The composition of claim 1 wherein the composition also comprises from about 0.1% to about 99% by weight of the personal care composition of a compatible solvent or solvent mixture.

5. The composition of claim 4 wherein the solvent or solvent mixture is selected from the group consisting of water, water-lower alkanols mixtures, polyhydric alcohols having from 3 to 6 carbon atoms and from 2 to 6 hydroxyl groups, and mixtures thereof.

6. The composition of claim 5 wherein the solvent or solvent mixture is selected from the group consisting of water, propylene glycol, water-glycerine, sorbitol-water, water-ethanol, and mixtures thereof.

7. The composition of claim 2 wherein the composition also comprises from about 0.1% to about 99% by weight of the personal care composition of a compatible solvent or solvent mixture.

8. The composition of claim 1 wherein the hydrophobically modified polysaccharide backbone is selected from the group consisting of hydroxyethylcellulose (HEC), hydroxypropylcellulose (HPC), methylcellulose (MC), hydroxypropylmethylcellulose (HPMC), ethylhydroxyethylcellulose (EHEC), and methylhydroxyethylcellulose (MHEC), and agar, dextran, locust bean gum, starch, guar, and their nonionic derivatives, and mixtures thereof.

9. The composition of claim 1 wherein the polysaccharide backbone is HEC and the hydrophobic moiety is 3-butoxy-2-hydroxypropyl.

10. The composition of claim 4 wherein composition also contain an effective viscosifying amount of a salt.

11. A hair or skin care composition comprising a solvent and an effective amount of the personal care composition of claim 7.

12. A shampoo comprising an effective amount of the personal care composition of claim 4.

13. A conditioner comprising an effective amount of the personal care composition of claim 4.

14. A shampoo-conditioner comprising an effective amount of the composition of claim 1.

15. A sun care product comprising a solvent and an effective amount of personal care composition of claim 1.

16. A shower gel comprising an effective amount of cleaning composition of claim 1.

17. A soap comprising an effective amount of the personal care composition of claim 1.

18. A hair styling gel composition comprising an effective amount of the personal care composition of claim 1.

19. A hair styling gel composition comprising an effective amount of the personal care composition of claim 4.

20. A hair anti-dandruff composition comprising solvent and effective amount of the personal care composition of claim 7.

21. A hair growth promoter composition comprising an effective amount of the personal care composition of claim 1.

22. A hair colorant composition comprising an effective amount of the personal care composition of claim 1.

23. A hair bleaching agent composition comprising an effective amount of the personal care composition of claim 1.

24. A hair anti-frizzing agent composition comprising an effective amount of the personal care composition of claim 1.

25. A hair relaxer composition comprising an effective amount of the personal care composition of claim 1.

26. A dentifrice composition comprising an effective amount of a personal care composition comprising:

a. from about 0.1% to about 99% by weight of a vehicle system which comprises a hydrophobically modified nonionic water soluble polysaccharide polymer having a hydrophilic portion which comprises a water soluble polysaccharide polymer backbone and a hydrophobic moiety which comprises 3-alkoxy-2-hydroxypropyl group wherein the alkyl moiety is a straight or branch chain having 2–6 carbon atoms, and wherein the ratio of the hydrophilic portion to the hydrophobic portion of the polymer is from about 2:1 to 1000:1, and b. at least one active personal care dentifrice ingredient.

27. A mouth wash composition comprising an effective amount of a personal care composition comprising:

a. from about 0.1% to about 99% by weight of a vehicle system which comprises a hydrophobically modified nonionic water soluble polysaccharide polymer having a hydrophilic portion which comprises a water soluble polysaccharide polymer backbone and a hydrophobic moiety which comprises 3-alkoxy-2-hydroxypropyl group wherein the alkyl moiety is a straight or branch chain having 2–6 carbon atoms, and wherein the ratio of the hydrophilic portion to the hydrophobic portion of the polymer is from about 2:1 to 1000:1, and b. at least one active personal care mouth wash ingredient.

28. A denture adhesive composition comprising an effective amount of a personal care composition comprising:

a. from about 0.1% to about 99% by weight of a vehicle system which comprises a hydrophobically modified nonionic water soluble polysaccharide polymer having a hydrophilic portion which comprises a water soluble polysaccharide polymer backbone and a hydrophobic moiety which comprises 3-alkoxy-2-hydroxypropyl group wherein the alkyl moiety is a straight or branch chain having 2–6 carbon atoms, and wherein the ratio of the hydrophilic portion to the hydrophobic portion of the polymer is from about 2:1 to 1000:1, and b. at least one active personal care denture adhesive ingredient.

29. A shaving product composition comprising an effective amount of the personal care composition of claim 1.

30. A lubricating gel composition comprising an effective amount of the personal care composition of claim 1.

31. A spermicide gel composition comprising an effective amount of the personal care composition of claim 1.

32. A beauty aid composition comprising an effective amount of the personal care composition of claim 1.

33. An underarm solid stick composition comprising an effective amount of a personal care composition comprising a. from about 0.1% to about 99% by weight of a vehicle system which comprises a hydrophobically modified nonionic water soluble polysaccharide polymer having a hydrophilic portion which comprises a water soluble polysaccharide polymer backbone and a hydrophobic moiety which comprises 3-alkoxy-2-hydroxypropyl group wherein the alkyl moiety is a straight or branch chain having 2–6 carbon atoms, and wherein the ratio of the hydrophilic portion to the hydrophobic portion of the polymer is from about 2:1 to 1000:1, and b. at least one active personal care underarm solid stick ingredient.

34. An underarm gel composition comprising an effective amount of a personal care composition comprising:

a. from about 0.1% to about 99% by weight of a vehicle system which comprises a hydrophobically modified nonionic water soluble polysaccharide polymer having a hydrophilic portion which comprises a water soluble polysaccharide polymer backbone and a hydrophobic moiety which comprises 3-alkoxy-2-hydroxypropyl group wherein the alkyl moiety is a straight or branch chain having 2–6 carbon atoms, and wherein the ratio of the hydrophilic portion to the hydrophobic portion of the polymer is from about 2:1 to 1000:1, and b. at least one active personal care underarm gel ingredient.

35. An underarm liquid composition comprising an effective amount of a personal care composition comprising:

a. from about 0.1% to about 99% by weight of a vehicle system which comprises a hydrophobically modified nonionic water soluble polysaccharide polymer having a hydrophilic portion which comprises a water soluble polysaccharide polymer backbone and a hydrophobic moiety selected from the group consisting of $C_3$–$C_7$ alkyl aryl alkyl, alkyl aryl groups and mixtures thereof, wherein the ratio of the hydrophilic portion to the hydrophobic portion of the polymer is from about 2:1 to 1000:1, and b. at least one active personal care underarm liquid ingredient.

36. The underarm liquid composition of claim 35 wherein the at least one active personal care ingredient comprises an aerosol ingredient.

37. A cleansing composition comprising an effective amount of a composition of claim 1 comprising:

a. from about 0.1% to about 99% by weight of a vehicle system which comprises a hydrophobically modified nonionic water soluble polysaccharide polymer having a hydrophilic portion which comprises a water soluble polysaccharide polymer backbone and a hydrophobic moiety selected from the group consisting of $C_3$–$C_7$ alkyl aryl alkyl, alkyl aryl groups and mixtures thereof, wherein the ratio of the hydrophilic portion to the hydrophobic portion of the polymer is from about 2:1 to 1000:1, and b. at least one active personal care cleansing ingredient.

38. A hair grooming and hair detangler composition comprising an effective amount of a personal care composition comprising:

a. from about 0.1% to about 99% by weight of a vehicle system which comprises a hydrophobically modified nonionic water soluble polysaccharide polymer having a hydrophilic portion which comprises a water soluble polysaccharide polymer backbone and a hydrophobic moiety selected from the group consisting of $C_3$–$C_7$ alkyl, aryl alkyl, alkyl aryl groups and mixtures thereof, wherein the ratio of the hydrophilic portion to the hydrophobic portion of the polymer is from about 2:1 to 1000:1, and b. at least one active personal care hair grooming and hair detangler ingredient.

39. A razor blade lubrication strip composition comprising an effective amount of a personal care composition comprising:

a. from about 0.1% to about 99% by weight of a vehicle system which comprises a hydrophobically modified nonionic water soluble polysaccharide polymer having a hydrophilic portion which comprises a water soluble polysaccharide polymer backbone and a hydrophobic moiety selected from the group consisting of $C_3$–$C_7$ alkyl aryl alkyl, alkyl aryl groups and mixtures thereof, wherein the ratio of the hydrophilic portion to the hydrophobic portion of the polymer is from about 2:1 to 1000:1, and b. at least one active personal care razor blade lubrication strip ingredient.

40. A cleansing tissue composition comprising an effective amount of a personal care composition comprising:

a. from about 0.1% to about 99% by weight of a vehicle system which comprises a hydrophobically modified nonionic water soluble polysaccharide polymer having a hydrophilic portion which comprises a water soluble polysaccharide polymer backbone and a hydrophobic moiety selected from the group consisting of $C_3$–$C_7$ alkyl, aryl alkyl, alkyl aryl groups and mixtures thereof, wherein the ratio of the hydrophilic portion to the hydrophobic portion of the polymer is from about 2:1 to 1000:1, and b. at least one active personal care cleansing tissue ingredient.

41. The personal care composition of claim 1, wherein the hydrophobic moiety is attached to the backbone by a linkage group selected from the class consisting of ether, ester, and urethane.

42. The personal care composition of claim 41, wherein the linkage group is an ether.

43. A personal care composition comprising:

a. from about 0.1% to about 99% by weight of a vehicle system which comprises a hydrophobically modified nonionic water soluble polysaccharide polymer having a hydrophilic portion which comprises a water soluble polysaccharide polymer backbone and a hydrophobic moiety which comprises 3-alkoxy-2-hydroxypropyl group wherein the alkyl moiety is a straight or branch chain having 2–6 carbon atoms, and wherein the ratio of the hydrophilic portion to the hydrophobic portion of the polymer is front about 2:1 to 1000:1, and b. at least one active personal care ingredient, wherein the composition is an oil-in-water or water-in-oil emulsion.

44. A personal care cleansing composition comprising:

a. from about 0.1% to about 99% by weight of a vehicle system which comprises a hydrophobicity modified nonionic water soluble polysaccharide polymer having a hydrophilic portion which comprises a water soluble polysaccharide polymer backbone and a hydrophobic moiety which comprises 3-alkoxy-2-hydroxypropyl group wherein the alkyl moiety is a straight or branch chain having 2–6 carbon atoms, and wherein the ratio of the hydrophilic portion to the hydrophobic portion of the polymer is from about 2:1 to 1000:1, and b. at least one active personal care cleansing ingredient.

* * * * *